United States Patent
Calvin et al.

(10) Patent No.: US 8,060,316 B2
(45) Date of Patent: Nov. 15, 2011

(54) METHODS, DATA STRUCTURES, AND SYSTEMS FOR CLASSIFYING MICROPARTICLES

(75) Inventors: Edward A. Calvin, Austin, TX (US); Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 1476 days.

(21) Appl. No.: 11/461,582

(22) Filed: Aug. 1, 2006

(65) Prior Publication Data

US 2010/0241360 A1    Sep. 23, 2010

Related U.S. Application Data

(60) Provisional application No. 60/704,699, filed on Aug. 2, 2005.

(51) Int. Cl.
*G01N 33/48* (2006.01)
(52) U.S. Cl. .......................................................... 702/19
(58) Field of Classification Search ..................... 702/19
See application file for complete search history.

(56) References Cited

U.S. PATENT DOCUMENTS

| | | | |
|---|---|---|---|
| 4,661,913 A | 4/1987 | Wu et al. | |
| 5,605,805 A | 2/1997 | Verwer et al. | |
| 5,627,040 A | 5/1997 | Bierre et al. | |
| 5,739,000 A | 4/1998 | Bierre et al. | |
| 5,981,180 A | 11/1999 | Chandler et al. | |
| 6,449,562 B1 | 9/2002 | Chandler et al. | |
| 2003/0009470 A1 | 1/2003 | Leary | |
| 2003/0182068 A1 | 9/2003 | Battersby et al. | |
| 2004/0059519 A1 | 3/2004 | Chandler et al. | |
| 2005/0123445 A1 | 6/2005 | Blecka et al. | |

FOREIGN PATENT DOCUMENTS

WO    00/67894    11/2000

OTHER PUBLICATIONS

International Search Report, PCT/US2006/029806, mailed Dec. 6, 2006.

*Primary Examiner* — Jerry Lin
(74) *Attorney, Agent, or Firm* — Fulbright & Jaworski LLP

(57) ABSTRACT

Methods, data structures, and systems for classifying particles are provided. In particular, the methods and systems are configured to acquire a first set of data corresponding to measurable parameters of a microparticle and identify a location of a look-up table to which the first set of data corresponds, wherein the look-up table is framed by values associated with at least one of the measurable parameters. Furthermore, the methods and systems are configured to determine whether the first set of data fits one or more predefined algorithms respectively indicative of a different microparticle classification associated with the identified location of the look-up table. The methods and systems are further configured to classifying the microparticle within at least one predefined categorization based upon the determination of whether the first set of data fits the one or more predefined algorithms.

20 Claims, 4 Drawing Sheets

METHODS, DATA STRUCTURES, AND SYSTEMS FOR CLASSIFYING MICROPARTICLES

PRIORITY CLAIM

The present application claims priority to U.S. Provisional Application No. 60/704,699 filed Aug. 2, 2005.

BACKGROUND OF THE INVENTION

1. Field of the Invention

This invention generally relates to methods, data structures, and systems for classifying microparticles. Certain embodiments relate to methods for classifying a microparticle using data acquired for the microparticle in combination with a lookup table and one or more algorithms associated with different microparticle classifications.

2. Description of the Related Art

The following descriptions and examples are not admitted to be prior art by virtue of their inclusion within this section.

Generally, flow cytometers provide measurements of fluorescence intensity and other optical properties of microparticles (e.g., laser excited polystyrene beads) as they pass linearly through a flow chamber. A variety of measurements may be performed including, but not limited to, the level of light scattered by the microparticle, the measure of electrical impedance of the microparticle, and one or more measurements of fluorescence of the microparticle. These and any other measurements may be performed by different "channels" of the system (e.g., reporter channels and classification channels), which include a detector and possibly other components (e.g., optical components, electronic components, etc.) coupled to the detector.

Often microparticles may be classified by their one or more of their measurement values, each value corresponding to a different "parameter" (examples of which are noted above) of the microparticle. For example, one common method of classifying microparticles is to graph measurement values in a classification space (e.g., a bitmap) and determine if the graphed location is positioned within a predetermined area of the classification space that corresponds to a particular classification of microparticles. Such a process is referred to herein as a bitmap-based conventional classification method. Unfortunately, the process has its drawbacks. In particular, graphical representation of the classification schemes using this methodology is not easily extended to more than two parameters.

One specific problem encountered in extending the aforementioned classification method to more than two parameters is that the size of the graph scales linearly with the resolution of each parameter used to classify the microparticle, and exponentially according to the number of parameters. For example, if a two-dimensional bitmap has a combined size of 100 units (i.e., 10 units×10 units), then a three-dimensional bitmap will have a combined size of 1,000 units and a four-dimensional bitmap will have a combined size of 10,000 units. Such exponential increases, in some cases, may be completely prohibitive for some system memory capacity. Also, it is noted that parameters of data acquired for microparticles by flow cytometry often have a combined size that is much higher than 100 possible units and typically include three or more parameters. Furthermore, creating bitmaps in more than two dimensions is much more difficult than in two dimensions, since representing a "more than two"-dimensional bitmap in a two-dimensional structure such as a piece of paper or a computer display requires some sacrifice in fidelity to the actual data.

Accordingly, it would be desirable to develop methods, data structures, and systems for classifying particles that can be easily extended beyond more than two parameters, that do not expand memory usage exponentially with each additional parameter, and are structured to minimize the processing time in which particle classification is performed.

SUMMARY OF THE INVENTION

The following description of various embodiments of methods, data structures, and systems is not to be construed in any way as limiting the subject matter of the appended claims.

An embodiment of a computer-implemented method includes acquiring a first set of data corresponding to measurable parameters of a microparticle and identifying a location of a look-up table to which the first set of data corresponds, wherein the look-up table is framed by values associated with at least one of the measurable parameters. Furthermore, the method includes determining whether the first set of data fits one or more predefined algorithms, wherein each of the one or more predefined algorithms is respectively indicative of a different microparticle classification of a plurality of microparticle classifications associated with the identified location of the look-up table. The method further includes classifying the microparticle within at least one predefined categorization based upon the determination of whether the first set of data fits the one or more predefined algorithms. This embodiment of the method may include any other steps described herein.

An embodiment of a system includes a processor, a look-up table framed by one or more measurable parameters of microparticles, and program instructions which are executable by the processor for performing the steps of the aforementioned computer-implemented method. This embodiment of a system may be further configured as described herein. In addition, the data structure of the look-up table may be further configured as described herein.

Another embodiment of a computer-implemented method includes acquiring a first set of data corresponding to measurable parameters of a microparticle and creating a second data set including one or more umbrella values respectively correlating to one or more distinct values of the first set of data. Each of the umbrella values represents a range of possible values for a corresponding measurable parameter. The method further includes identifying a location of a look-up table to which the second data set corresponds, wherein the look-up table is framed by umbrella values of at least one of the measurable parameters. In addition, the method includes determining whether the first set of data fits a predefined algorithm indicative of a microparticle classification associated with the identified location of the look-up table and classifying the microparticle within at least one predefined categorization based upon such a determination. This embodiment of the method may include any other steps described herein.

BRIEF DESCRIPTION OF THE DRAWINGS

Other objects and advantages of the invention will become apparent upon reading the following detailed description and upon reference to the accompanying drawings in which.

Figure 1:
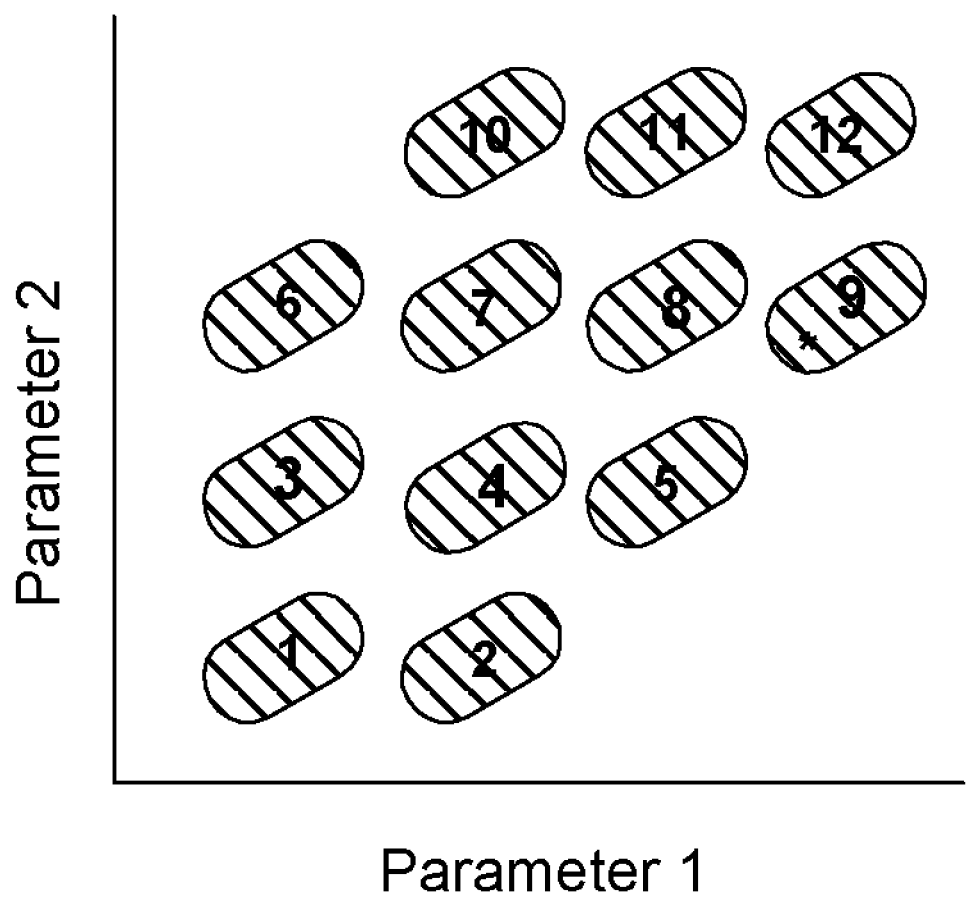
FIG. 1 is a two-dimensional graph that includes classification spaces corresponding to populations of which microparticles may be members.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The term "microparticle" is used herein to generally refer to particles, microspheres, polystyrene beads, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substrates or substances known in the art. Any of such terms may be used interchangeably herein. The methods, data structures, and systems described herein may be used for classification of any type of microparticles. In some cases, the methods, data structures, and systems described herein may be particularly used for microparticles serving as vehicles for molecular reactions. Exemplary molecular reaction microparticles which are used in flow cytometry include xMAP® microspheres, which may be obtained commercially from Luminex Corporation of Austin, Tex.

As used herein, the term "classification" is generally defined as determining the identity of individual microparticles in a sample. The identity relates to the population to which individual microparticles belong. Such classification is of particular importance since often a sample will be analyzed with multiple, different populations of microparticles in a single experiment of the sample. In particular, different populations of microparticles typically have at least one different characteristic such as the type of substance coupled to the microparticles and/or the quantity of substance(s) coupled to the microparticles such that the presence of different types and/or quantities of analytes within the sample can be detected and/or quantified in a single experiment. To interpret the measurement results, the identity or classification of individual microparticles in the sample may be determined such that the measurement values may be correlated to the properties of the individual microparticles. In this manner, the measurement values associated with the different populations of microparticles can be distinguished and respectively attributed to the analytes of interest.

Systems that may be configured to perform one or more of the processes described herein include, but are not limited to, the Luminex® 100™, the Luminex® HTS, the Luminex® 100E, Luminex® 200™, and any further add-ons to this family of products that are available from Luminex Corporation of Austin, Tex. One general example of such systems is described further herein in reference to FIG. 5. However, it is to be understood that the methods, data structures, and systems described herein may use or may be configured to use microparticle data acquired by any measurement system. Examples of measurement systems include flow cytometers and fluorescent imaging systems. In addition, although various parameters are described herein that can be used for microparticle classification, it is to be understood that the embodiments described herein may use any measurable parameter of microparticles that can be used to distinguish different populations of the microparticles. Furthermore, the methods, data structures, and systems described herein are not limited to microparticle classification. In particular, the embodiments described herein may be equally applied to determining other parameters of microparticles such as, but not limited to, the identity or quantity of a reaction product present on the microparticles or in the sample.

Turning to the drawings, FIG. 1 illustrates an exemplary classification space which may be used to classify microparticles in a conventional manner. The process includes acquiring data for microparticles using a flow cytometer or other suitable device and using the data for classification. In particular, the method typically includes plotting measurement data for two parameters on a graph having two axes each corresponding to a different parameter (such as shown by axis titles Parameter 1 and Parameter 2 in FIG. 1). The graph also includes different classification areas (e.g., areas 1-12 shown in FIG. 1), each corresponding to a different population of microparticles. The location of a data point in the graph corresponding to the measured parameters of a microparticle determines the microparticle's membership in one of the populations. For example, as shown in FIG. 1, a single data point corresponding to values of two parameters acquired for a single microparticle is shown by an asterisk (*). Because the data point lies within the boundaries of area 9 (represented in the graph as the cross-hatched space labeled with the numeral 9), the microparticle is classified as being a member of the population corresponding to area 9. If the data point instead is located in the white space in the graph outside of areas 1-12, then the microparticle is classified as not being a member of any area and is thereby not classified as belonging to any population.

The methods and systems described herein perform microparticle classification in a manner different than that described above. In particular, the embodiments described herein utilize a look-up table (LUT) to narrow a search of classification populations to which a microparticle may belong and subsequently process data acquired for the microparticle in one or more predefined algorithms associated with an identified location of the look-up table.

Figure 2:
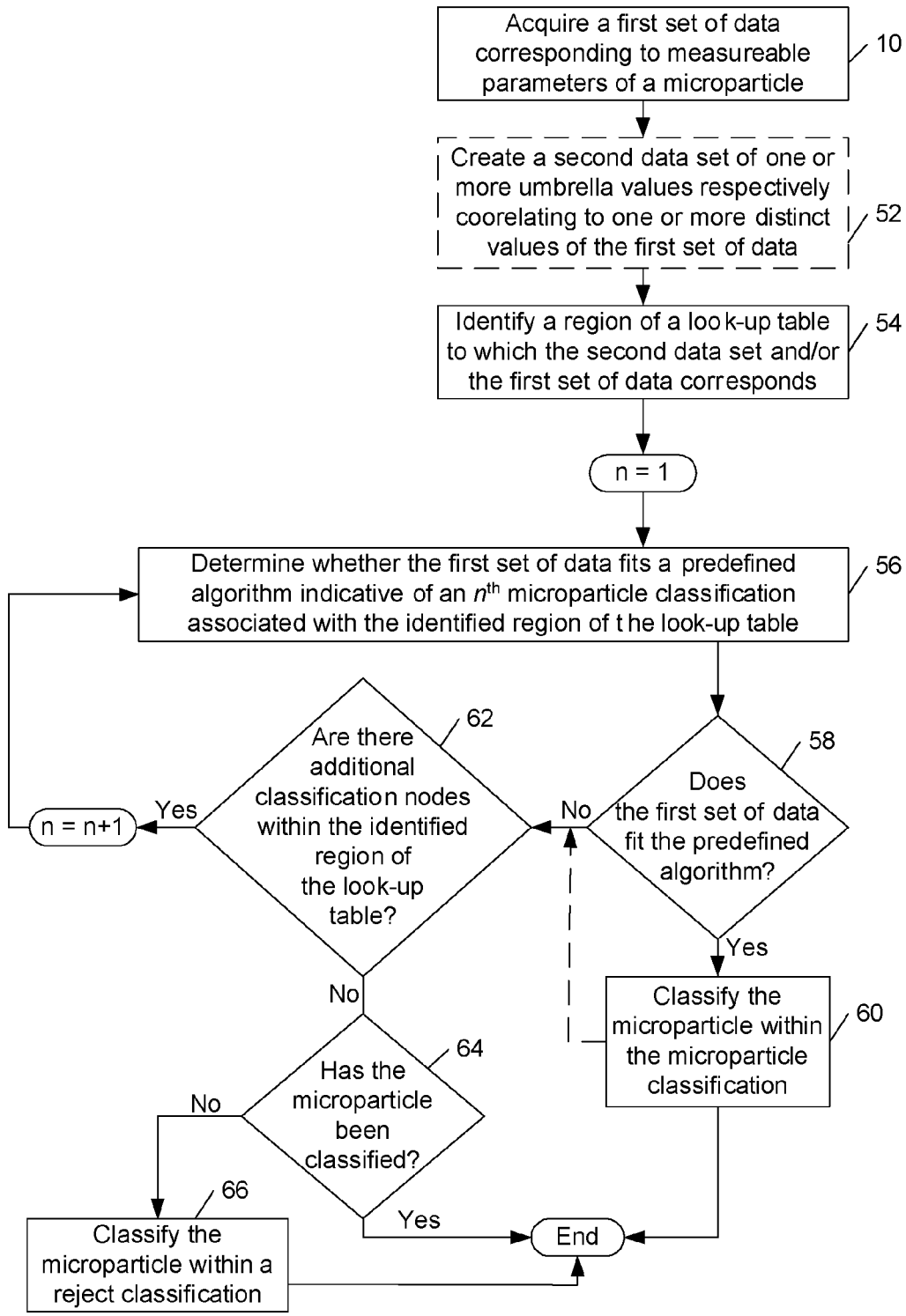
FIG. 2 illustrates a flow chart of a method for classifying a microparticle

A flowchart outlining exemplary steps of such a method is shown in FIG. 2. As described in more detail below, the algorithms which are used to define the microparticles classifications may, in some embodiments, be complex (e.g., the algorithms may relate more than 2 measurement parameters of a microparticle) and, therefore, may be best implemented through a computer. As such, the systems and storage mediums described herein, such as described in reference to FIG. 5, may include program instructions which are executable by a processor and which are configured to perform the processes depicted in FIG. 2. Therefore, the methods described in reference to FIG. 2 may be referred to as "computer-implemented methods" and, thus, the terms "method" and "computer-implements method" may be used interchangeably herein. It is noted that the computer-implemented methods and program instructions of the systems described herein may, in some cases, be configured to perform processes other than those associated with microparticle classification and, therefore, the computer-implemented methods and program instructions of systems described herein are not necessarily limited to the depiction of FIG. 2. Furthermore, although the steps described herein are described with respect to classification of "a microparticle," it is to be understood that any or all of the steps of the method embodiments described herein may be performed for one or more microparticles in a set (e.g., some or all of the microparticles in a set).

As shown in FIG. 2, the methods and program instructions of the systems described herein may include block 10 in which a first set of data corresponding to measurable parameters of a microparticle. Such a data set may be those obtained by a flow cytometer or other suitable device. The data may be acquired by measuring the data for individual microparticles using the flow cytometer or by requesting and receiving the data from the flow cytometer. In this manner, the method may be performed by the measurement system itself (e.g., by a processor of the measurement system) or by a system (e.g., a processor of a stand-alone computer system) coupled to the measurement system. In any case, the data set may, in some embodiments, include measurements of several different parameters including but not limited to those used to classify the microparticle. For example, the first set of data may include measurements of fluorescence, light scatter, electrical impedance, or any other measurable property of the microparticle.

In some embodiments, the method and program instructions of the systems described herein may continue to block 52 as shown in FIG. 2 to create a second data set having one or more umbrella values respectively correlating to one or more distinct values of the first set of data. Such a step may advantageously reduce the resolution of the measurements within the first set of data to coincide with the scale of measurement parameter values used to frame a look-up table. As described in more detail below, the look-up table is a data structure used to narrow the search of a microparticle classification to which to categorize the microparticle. A look-up table framed by values of relatively low resolution may allow the table to be sized with a smaller number of units which, in turn, limit the size of the memory needed to characterize the table. Limiting the size of the memory for the look-up table may be advantageous in some cases, particularly for reducing the cost of a system. Although creating a second set of data with values of reduced resolution relative to corresponding values of the first set of data may be advantageous in some cases, it is noted that creation of the second data set in the methods described herein is optional and, consequently, block 52 has been outlined by a dotted line. In particular, the methods described herein do not necessarily need to include the creation of a data set with reduced resolution values. Rather, the method may omit block 52 and continue to block 54 to identify a location of a look-up table to which the first set of data corresponds as described in more detail below.

In some embodiments, the creation of the second data set may include replicating one or more values of the first set of data and reducing the resolution of one or more of the replicated values. In some cases, the resolution of all of the replicated values may be reduced. In other cases, however, less than all of the replicated values may be reduced. As such, although the second data set is created to include values of reduced resolution, the second data set is not necessarily restricted from also including values which have not been reduced in resolution (i.e., relative to corresponding values in the first set of data). For example, in some embodiments, only one of the measurement parameters framing the look-up table may include a scale of low resolution and, therefore, it may only be pertinent to reduce the resolution of replicated values associated with that measurement parameter. Other scenarios may warrant reducing the resolution of a fraction of the replicated values and, therefore, the methods described herein are not necessarily limited to such an example.

In some embodiments, the second data set may include values associated with all of the values acquired for the first data set. In other embodiments, the second data set may include fewer values than those acquired for the first set of data. For instance, the method and program instructions described herein may, in some embodiments, be configured to create a second data set with only values associated with measurement parameters framing the look-up table. Other scenarios may warrant the second data set to include a fraction of the values acquired for the first set of data and, therefore, the methods described herein are not necessarily limited to the aforementioned example.

In any case, the values of reduced resolution within the second data set (i.e., relative to the corresponding values in the first set of data) may be referred to herein as "umbrella values". Alternatively stated, the term "umbrella value" may generally refer to a value representing a range or span of possible values for a corresponding measurement parameter. In contrast, values whose resolution has not been reduced, such as those in the first set of data, may be referred to herein as "distinct values" and/or "measurement values". In some cases, creating the second data set may include rounding one or more replicated values of the first set of data to the nearest integer value. For example, measurement values of 1.07 and 1.09 may be both represented by an umbrella value of 1.1. In this manner, each of the rounded values may generally represent a range of possible measurement values less than, greater, or midway from the rounded integer to the next integer. For instance, in the aforementioned embodiments, an umbrella value of 1.1 may represent measurement values between 1.01 and 1.10. In other embodiments, an umbrella value of 1.1 may represent measurement values between 1.10 and 1.19 or measurement values between 1.05 and 1.14. In general, the ranges of measurement values an umbrella value may represent may depend on the design specifications set up for the method and, in some embodiments, the design specifications of the program instructions configured to perform such a process step.

In other cases, the second data set may include umbrella values representing ranges of integers for a measurement parameter. For example, as shown in Table 1, discrete values associated with Parameter 1 in a first set of data may be referenced by any one of four umbrella values in a second data set. It is noted that Table 1 is merely an exemplary correlation of distinct and umbrella values. The range of distinct values and the number of selected umbrella values for a measurement value may differ among different set ups of methods and program instructions.

TABLE 1

| Distinct Measured Values of Parameter 1 | Umbrella Values of Parameter 1 |
| --- | --- |
| 1.00-25.99 | 1 |
| 26.00-50.99 | 2 |
| 51.00-75.99 | 3 |
| 76.00-100.00 | 4 |

Furthermore, although the ranges of discrete values shown in Table 1 are equally segregated among the umbrella values (i.e., 25 discrete values for each umbrella value), it is to be understood that each umbrella value may correspond to any number of discrete values. In other words, the ranges of distinct values respectively associated with umbrella values for a measurement parameter may not necessarily be uniform.

In some cases, the degree to which each discrete value is reduced in resolution may vary depending on, for example, characteristics of the microparticle classifications, characteristics of the microparticle populations, and/or characteristics of individual microparticles in the populations.

In any case, the resolution of values corresponding to different measurement parameters may, in some embodiments, be reduced in a similar manner for the second data set. In particular, distinct values corresponding to different measurement parameters may be either rounded to the nearest integer or assigned values for integer ranges to create the second data set. In other embodiments, distinct values corresponding to different measurement parameters may be reduced in different manners for the second data set. In any case, the number of umbrella values for different measurement parameters may be the same or different.

Turning back to FIG. 2, the methods and program instructions described herein may be configured to continue to block 54 to identify a location of a look-up table to which the second data set and/or the first set of data corresponds. More specifically, if block 52 is included in the process, then a location of the look-up table to which the second data set corresponds will be identified with respect to block 54. It is noted that since the second data set includes values corresponding to measured values in the first set of data, the location of the look-up table identified with respect to block 54 in such an embodiment will correspond to the first set of data as well as the second data set. However, in embodiments in which block 52 is omitted from the process, the location of the look-up table identified with respect to block 54 will only correspond to the first set of data since the second data set was not created.

In embodiments in which block 52 is omitted from the process, block 54 may generally include indexing the measured values from the first set of data which are associated with the parameters framing the look-up table, in effect locating a point as an "identified location" within the look-up table to which the first set of data corresponds. In some cases, methods which include block 52 may also be configured to locate a point as an "identified location" within the look-up table. In particular, if the scale resolution for each of the measurement parameters framing the look-up table is the same as the resolution of the corresponding values in the second data set, then block 54 may include indexing such values from the second data set to identify a location or, more specifically, a point within the look-up table to which the second data set corresponds. For example, if the umbrella values within the second data set represent integers rounded from the distinct values of the first set of data and the scale resolution of the corresponding measurement parameter/s framing the look-up table is at least high enough to distinguish individual integers, then indexing such values will culminate in a point in the look-up table. It is noted that such pinpointing within the look-up table may also include indexing distinct values from the second data set as long as the scale resolution of the corresponding measurement parameter/s are the same as the distinct values.

Figure 3:
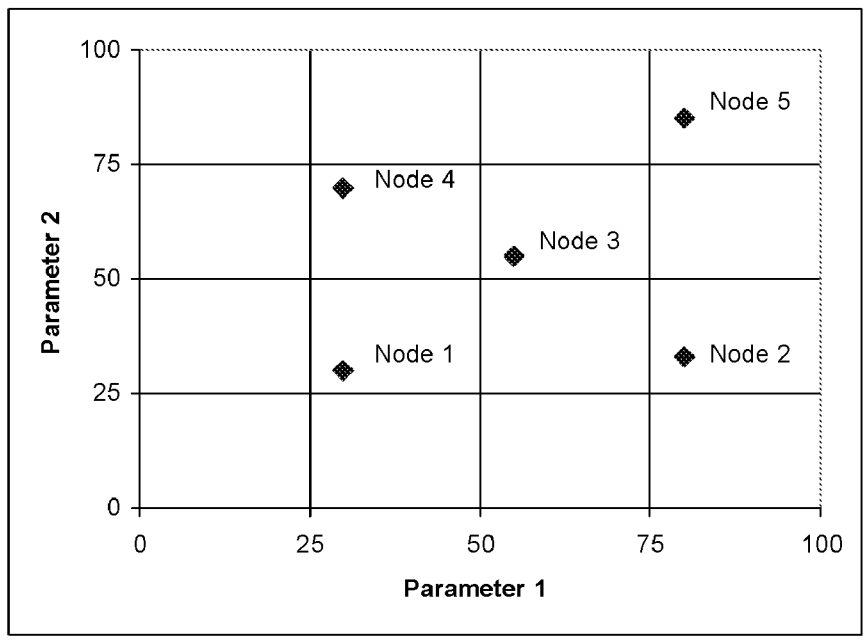
FIGS. 3 and 4 are schematic diagrams illustrating different embodiments of a lookup table.

An exemplary embodiment of a look-up table in which points may be identified as locations which correspond to values of a second data set is shown in FIG. 3. In particular, FIG. 3 illustrates an exemplary look-up table framed by two measurement parameters, the scales of which range from 0 to 100 and are limited to integer values. It is noted that a variety of configurations for look-up tables may be used for the methods described herein. In particular, as noted above, the scales of the measurement parameters framing a look-up table may be discrete values, integers, or values representing ranges of integers, depending on the desired resolution. In addition, the scales for the different measurement parameters framing the look-up table may be the same or different. Furthermore, the look-up tables described herein may be framed by any number of measurement parameters. As will be described in more detail below, the methods described herein may be particularly applicable for look-up tables framed by more than two measurement parameters. As such, look-up tables for the methods described herein are not necessarily limited to the depiction of the example in FIG. 3.

In general, identifying a location of the look-up table depicted in FIG. 3 may include indexing integer umbrella values associated with Parameters 1 and 2. As will be described in more detail below in reference to block 56, if an identified location coincides with one of nodes 1-5, then an algorithm associated with the node may be processed with the measured values of the first set of data to determine whether the particle may be classified within the microparticle classification corresponding to the node. In contrast, if the identified location does not coincide one of nodes 1-5, then the particle will be categorized within a reject classification. Such a determination of classification for the methods described herein changes when a coarse location of a look-up table comprising multiple nodes is identified to correspond with a set of data as described in more detail below.

Regardless, narrowing the search for a microparticle classification to test using the look-up tables described herein may save time relative to iteratively processing through each microparticle classification of a sample to determine the classification of a particle (which is also described in more detail below). It is noted for clarification purposes that nodes 1-5 in FIG. 3 signify different microparticle classifications with respect to the parameters framing the look-up table and, thus, are not necessarily identified locations of the look-up table corresponding to a first and/or second set of data. In addition, as will be described in more detail below, nodes 1-5 may be larger or smaller than those depicted in FIG. 3.

As noted above, coarse locations of a look-up table may be identified as corresponding to a set of data for block 54. In particular, block 54 may include indexing umbrella values which represent ranges of integers in relation to a relatively low resolution scale of the measurement parameters framing a look-up table to identify a block location of the look-up table. More specifically, the scale of the look-up table may include a relatively low resolution such that values on the scale are correlated to rows and columns of the look-up table. In such cases, the size of the look-up tables for given breadths of the measurement parameters may be smaller than those with integer value scales (such as shown in FIG. 3) and especially relative to those with scales which have not been reduced in resolution. As a consequence, memory size of the look-up tables may be reduced.

An exemplary look-up table in which coarse locations may be identified as locations which correspond to values of a second data set is shown in Table 2. In particular, Table 2 illustrates an exemplary look-up table framed by two measurement parameters, the scales of which range from 1 to 4, each correlating to a different range of integers for the respective measurement parameters. The look-up table of Table 2 has only 16 locations in comparison to, for example, 10,000 elements (100×100 units of each of the measurement parameters) that may be included in a full-resolution look-up table of the original values of the two parameters in some embodiments.

TABLE 2

|Parameter 2|Parameter 1 | | | |
|---|---|---|---|---|
| | 1 | 2 | 3 | 4 |
| 4 | No Node | No Node | No Node | Node 5 |
| 3 | No Node | Node 3 | Node 4 | No Node |
| 2 | No Node | Node 1 | No Node | Node 2 |
| 1 | No Node | No Node | No Node | No Node |

As with the look-up table depicted in FIG. 3, the look-up table of Table 2 may be used to narrow the search for a microparticle classification to which a particle may be categorized. In particular, in some embodiments, some of the coarse locations may include a node associated with a microparticle classification and, therefore, the identification of a location with a node may facilitate further investigation as to whether the particle may be categorized to the microparticle classification. In particular, when an identified location includes a node, an algorithm associated with the node may be processed with the measured values of the first set of data to determine whether the particle may be classified within the microparticle classification corresponding to the node. In contrast, if the identified coarse location does not include a node, then the particle will be categorized within a reject classification. For example, using the look-up table of Table 2, if a particular data point has umbrella values for Parameter 1=2 and Parameter 2=1 (i.e., 2,1), the method may determine that the data point is not a member of any node since the coarse location of the look-up table corresponding to these umbrella values of the parameters is not associated with any nodes. If instead a data point has umbrella values of (2,2), then the method may process the data point to determine whether it is a potential member of node 1 but not of nodes 2-5. Consequently, narrowing the search for a microparticle classification to test using the look-up table in Table 2 may save time relative to iteratively processing through each of nodes 1-5 to determine the classification of a particle.

The coarse locations including nodes 1-5 in Table 2 are outlined in bold to distinguish their presence relative to the coarse locations which do not include nodes. As noted above, a variety of configurations for look-up tables may be used for the methods described herein and, as such, a look-up table configured for identification of coarse locations is not limited to Table 2. In particular, the scales for the different measurement parameters framing the look-up table may be the same or different. Furthermore, the look-up tables described herein may include any number of scale values for each of the measurement parameters (i.e., they are not limited to four values as depicted in Table 2) and may be framed by any number of measurement parameters. Moreover, the number and distribution of nodes may vary within look-up tables described herein. For example, all coarse locations of a look-up table may include a node in some embodiments.

In general, the number of nodes per coarse location may be used determine the "resolution" of the look-up table. For example, a look-up table having no more than one node included in each coarse location, such as described in reference to Table 2, has the highest useful resolution. A look-up table having such resolution, however, may in some embodiments be relatively large. For instance, for a set of microparticles that includes 1,000 different populations, a look-up table having no more than one node per coarse location needs a minimum of 1,000 coarse locations. In order to minimize the memory capacity needed to represent so many nodes, it may be advantageous to reduce the resolution of a look-up table such that multiple nodes are arranged within one or more coarse locations.

As such, another exemplary look-up table in which coarse locations may be identified as locations which correspond to values of a second data set is shown in Table 3. In particular, Table 3 illustrates an exemplary look-up table framed by two measurement parameters, the scales of which range from 1 to 4, each correlating to a different range of integers for the respective measurement parameters as in Table 2. Table 3 differs from Table 2, however, by having some coarse locations with multiple nodes (i.e., node sets). In particular, Table 3 illustrates four coarse locations each with a plurality of nodes. A plurality of nodes within a single coarse location is referred to herein as a "node set." More specifically, Table 3 includes four coarse locations with Node Sets 1-4. Table 3 also includes one coarse location with a single node referenced as Node 5 and 11 coarse locations with no nodes. Such a configuration may allow a look-up table of a given size to include a greater number of nodes, permitting a greater number of microparticle classifications to categorize a particle within a sample. In addition or alternatively, as noted above, a look-up table having multiple nodes within coarse locations may be configured with lower-resolution scales relative to look-up tables which only include one node per coarse location. As a consequence, memory size of such look-up tables may be reduced.

TABLE 3

| Parameter 2 | Parameter 1 | | | |
|---|---|---|---|---|
| | 1 | 2 | 3 | 4 |
| 4 | No Node | No Node | No Node | Node 5 |
| 3 | No Node | Node Set 3 | Node Set 4 | No Node |
| 2 | No Node | Node Set 1 | No Node | Node Set 2 |
| 1 | No Node | No Node | No Node | No Node |

As shown in Table 3, some of the coarse locations of the look-up table may include no nodes or a single node. The coarse locations including nodes 1-5 in Table 3 are outlined in bold to distinguish their presence relative to the coarse locations which do not include nodes. As noted above, a variety of configurations for look-up tables may be used for the methods described herein and, as such, a look-up table having multiple nodes within a coarse location is not limited to Table 3. In particular, the scales for the different measurement parameters framing the look-up table may be the same or different. Furthermore, the look-up tables described herein may include any number of scale values for each of the measurement parameters (i.e., they are not limited to four values as depicted in Table 3) and may be framed by any number of measurement parameters. Moreover, the number, size, shape, and distribution of nodes may vary within look-up tables described herein. For example, all coarse locations of a look-up table may include at least one node in some embodiments. In addition or alternatively, nodes may overlap including those within a single coarse location of a look-up table and those of different coarse locations. It is noted that if membership of a data point to one node is mutually exclusive to membership in another node, then the rules of each node may be defined to be non-overlapping.

Figure 4:
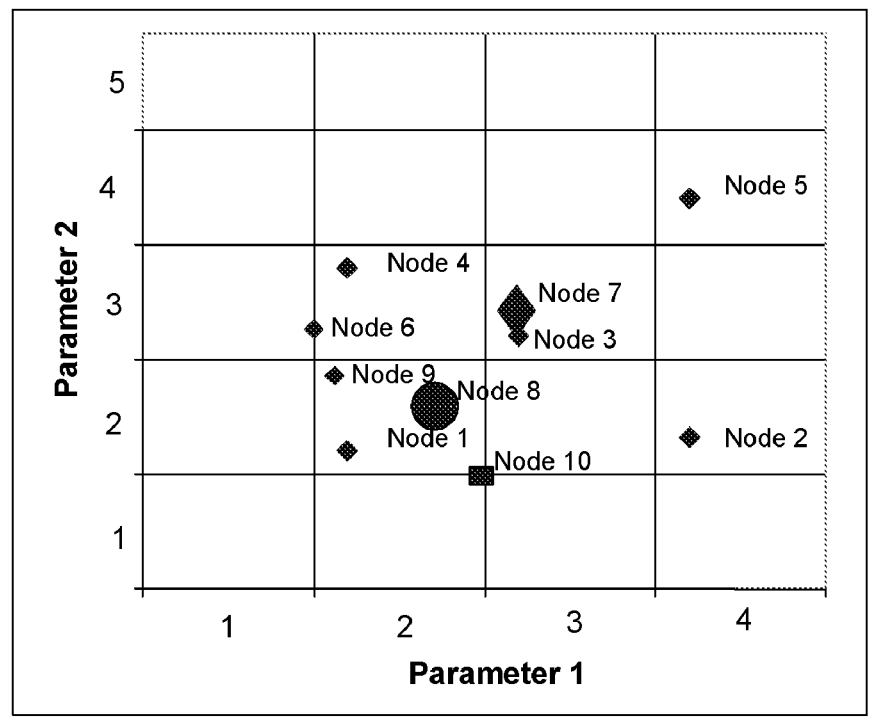

FIG. 4 illustrates yet another embodiment of a look-up table including multiple nodes arranged within coarse locations of the table. As with Table 3, FiG. 4 illustrates a look-up table having some locations with no nodes, some locations with one node, and other locations with more than one node. FIG. 4 differs from Table 3 by illustrating that the number, size, shape, and distribution of nodes may vary between look-up tables as well as within a single look-up table. In addition, FIG. 4 illustrates nodes may overlap boundaries of coarse locations and, therefore, may be associate with multiple locations, such as shown for nodes 6 and 10. Furthermore, FIG. 4 illustrates that nodes may, in some embodiments, overlap, such as depicted by nodes 3 and 7.

Turning back to FIG. 2, after the identification of the location within a look-up table, the method may continue to block 56 to determine whether the first set of data acquired in block 10 fits a predefined algorithm which is indicative of an $n^{th}$ microparticle classification associated the identified location, wherein n is set to equal 1 for the first processing of this step. As described above, the determination as to whether an identified location of a look-up table includes a microparticle classification to categorize a particle is denoted by the presence of a node. In particular, a node generally represents a microparticle classification to which the values of the measurement parameters framing the look-up table fit. It is noted, however, that presence of a node within an identified location of a look-up table does not necessarily indicate that the particle belongs to the associated microparticle classification. In particular, if the microparticle classification is characterized by measurement parameters other than those framing the look-up table or, more specifically, defining a detected node, a particle may or may not fit the algorithm defining the microparticle classification and, therefore, may or may not fit into such a classification. Alternatively stated, a microparticle classification may be defined by a plurality of measurement parameters, the dependence of which may not all be represented by the look-up table coarse parameters. For example, a microparticle classification may be defined by five different parameters, but the look-up table may be configured with four parameters (or less). As such, the values of the measurement parameters which are not represented in the look-up table may affect whether the particle may be categorized within a classification.

Although any number of parameters of a data set and virtually any mathematical or logical function may be used to characterize the nodes described in the look-up tables described herein, the look-up tables may, in some embodiments, be configured to characterize nodes with a number of parameters less than the parameters used to define a microparticle classification. Such a configuration may allow the look-up tables to provide a relatively good approximation as to whether a data set may belong to a particular classification and, therefore, provide a quick manner to narrow a search for a microparticle classification, but avoid the complexity of having too many parameters defining a node. As described with respect to block 56, the methods and program instructions described herein may be configured to provide a conclusive evaluation to determine the actual categorization of a particle through the use of algorithms specific to a microparticle classification after detection of a node.

In some cases, nodes may be characterized by attributes other than the measurement parameters of the microparticle classifications they are characterized to represent. Embodiments in which nodes are defined only by measurement parameters of the microparticle classifications they are characterized to represent may be referred to herein as having no attributes. In some cases, however, nodes may be defined by measurement parameters of the microparticle classifications they are characterized to represent as well as additional attributes. In some cases, attributes used to define a node may include broad ranges and, therefore, the data points for which a node covers within a look-up table may be broader than a characterization of a corresponding microparticle classification. Examples of attributes may include dimensions, orientation parameters, or locations with respect to other nodes.

In some embodiments, a node may be characterized by a single attribute. For example, a radius may be used to define a node if the center of the circle is assumed to be the center of the course location. In such cases, every microparticle that has a data point that lies within the radius of a node may be characterized by the node. The radii of all the nodes may be substantially the same or, alternatively, at least some of the nodes may have different radii. In other embodiments, two or more attributes may be associated with each node. For example, two or more dimensions may be used to characterize a node, thereby defining its shape. For instance, attributes may define two-dimensional shapes, such as a circle, ellipse, square, or rectangle, for example (the ellipse being defined by dimensions of major and minor axes and foci location). In addition, attributes may define three-dimensional shapes, such as a sphere, rectangular prism, or a cube, for example. Other complex shapes may be defined using two or more attributes as well to define boundaries of the data points of a node. Other attributes may also be used to define the orientation of a node within the look-up table (e.g., rather than having axes of the ellipse aligned with the axes of the measurement parameters of the look-up table). In another example, two attributes per node, one attribute for each parameter of the data set, may be used to set minimum and maximum limits of the node.

Although two-dimensional and three-dimensional nodes are described above, one of the strengths of the characterization of the nodes described herein is that characterization can be easily extended beyond three dimensions to any number of dimensions even if graphical representation of the data in three or more dimensions is not possible or practical. In addition, an advantage of the node/attribute based microparticle classification described herein is that the data need not be visualized graphically. In a bitmap-based conventional classification method, the data may be represented graphically in a bitmap during creation in order to generate boundaries for each area corresponding to a population of microparticles. The boundaries of the nodes described herein, however, are defined by measurement values of a microparticle classification and/or attributes which may form a shape within a look-up table. Visualization of such boundaries is not needed to create the area, therefore, graphical representation of the node is not needed.

Referring back to block 56 in FIG. 2, an algorithm indicative of microparticle classification may be defined based on a characteristic distribution of a population of microparticles. As described above, a microparticle may be categorized within a predefined classification by determining whether the microparticle is a member of a microparticle population corresponding to a node within an identified location of a look-up table. More specifically, the method may continue to block 58 in FIG. 2 to determine whether the first set of data fits within a predefined algorithm associated with the location of the look-up table identified in block 54. As shown in FIG. 2, upon detecting the first set of data fits the predefined algorithm, the method may continue to block 60 in which the microparticle is classified within the microparticle classification. From there, the evaluation of the classification of the particle may, in some embodiments, terminate, regardless of the number of nodes arranged within the identified location of the look-up table. In other embodiments, however, the process may continue to block 62 to determine whether there are other classification nodes within the identified location of the look-up table. Such an option is denoted by a dotted line in FIG. 2 to distinguish it as an alternative to the step of terminating the classification process after block 60.

As shown in FIG. 2, if the method continues along the alternative path from block 60 or the first set of data does not fit the predefined algorithm, the method continues to block 62 to determine whether any additional nodes are arranged within the identified location of the look-up table. Upon detecting no other nodes, the process continues to block 64 to determine whether the microparticle has been classified (such as in block 60). If the microparticle has been classified, the process terminates. If, however, the microparticle has not yet been classified, the microparticle is classified to a reject classification in block 66 and the process subsequently terminates. The reject classification referenced in block 66 may generally refer to a category of particles which cannot be readily assigned to known classifications.

As noted above, the methods and program instructions described herein may be particularly applicable to using look-up tables having multiple nodes within coarse locations of the tables. In some embodiments, the first set of data acquired in block 10 may be processed through algorithms of a plurality of the nodes to determine a classification for a microparticle. In particular, algorithms associated with the plurality of nodes may, in some embodiments, be processed sequentially until a classification for the particle can be determined. Such an embodiment may be advantageous for cases in which the microparticle classifications are mutually exclusive. In other embodiments, a plurality of the algorithms associated with the plurality of nodes may be processed to determine if the data set fits more than one of the classifications associated with the nodes. In such cases, the classifications may have overlapping characterizations. In embodiments in which a particle is classified to multiple categorizations, the method may further include determining which one of the plurality of predefined algorithms best fit the first set of data and subsequently cataloging the particle within the microparticle classification associated with the single predefined algorithm. Alternatively, method may include cataloging the particle as a member of multiple populations if the populations are not mutually exclusive.

In any case, upon determining there are additional classification nodes within the identified location of the look-up table, the method may increase the n factor by 1 and continue back to block 56 to determine whether the first set of data fits a predefined algorithm associated with another node within the identified location. Subsequently, the method may continue through blocks 58, 60, 62, 64, and 66 as described above. In general, the configuration of such steps allows locations of a look-up table including one or more nodes or no nodes to be evaluated for classifying a microparticle. As described above, the method may advantageously narrow the search of a classification to a select number of nodes such that time to classify a microparticle may be reduced relative to methods which would evaluate all possible classifications for a sample.

Figure 5:
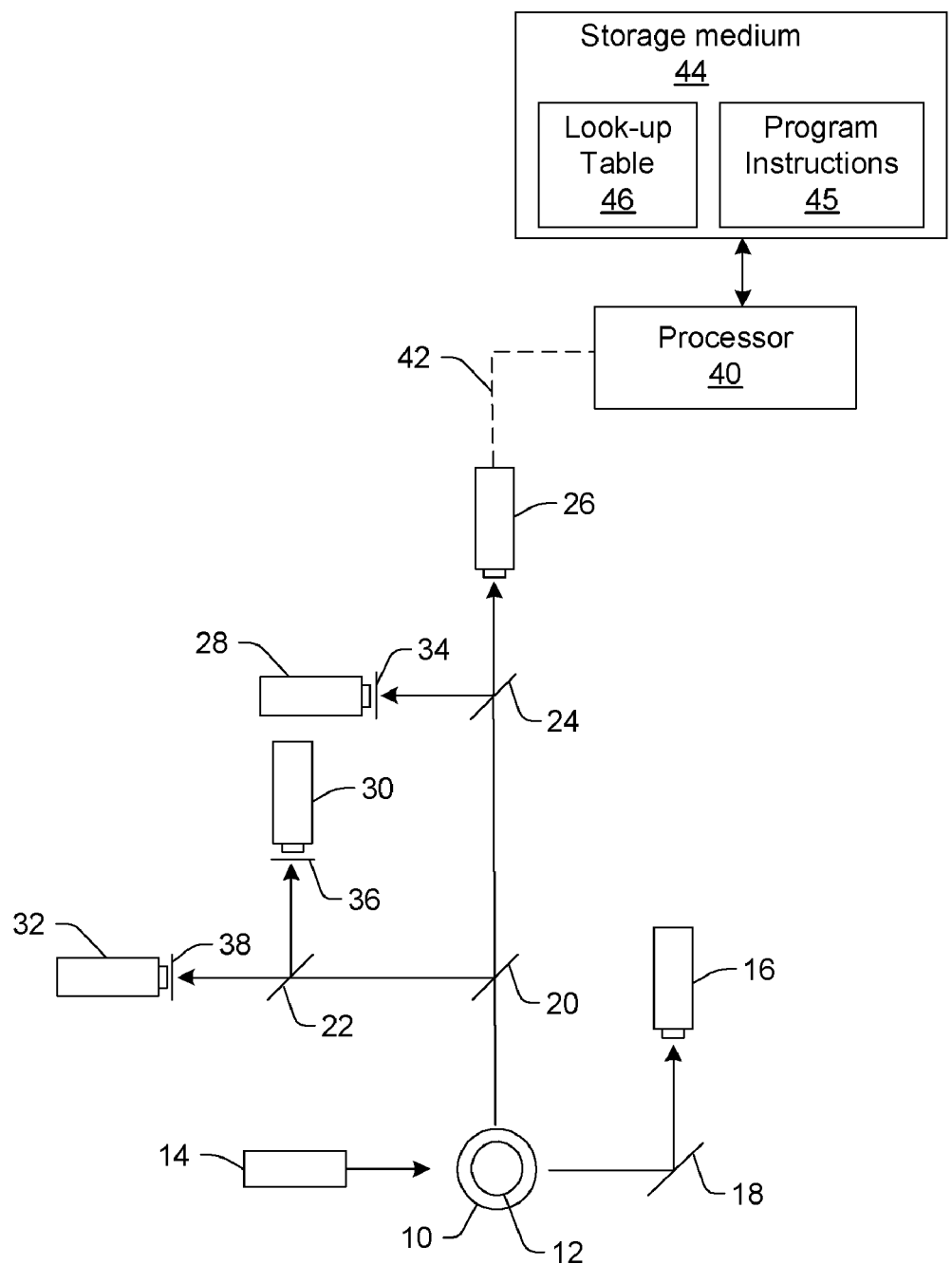
FIG. 5 is a schematic diagram illustrating one embodiment of a system configured to classify microparticles.

FIG. 5 illustrates an exemplary embodiment of a system configured to classify microparticles. It is noted that FIG. 5 is not drawn to scale. In particular, the scale of some of the elements of the figure is greatly exaggerated to emphasize characteristics of the elements. Some elements of the system have not been included in the figure for the sake of clarity. In FIG. 5, the system is shown along a plane through the cross-section of cuvette 10 through which microparticles 12 flow. In some embodiments, the cuvette may be a standard quartz cuvette such as that used in standard flow cytometers. Any other suitable type of viewing or delivery chamber, however, may also be used to deliver the sample for analysis.

The system includes light source 14. Light source 14 may include any appropriate light source known in the art such as a laser. The light source may be configured to emit light having one or more wavelengths such as blue light or green light. Light source 14 may be configured to illuminate the microparticles as they flow through the cuvette. The illumination may cause the microparticles to emit fluorescent light having one or more wavelengths or wavelength bands. In some embodiments, the system may include one or more lenses (not shown) configured to focus light from the light source onto the microparticles or the flowpath. The system may also include more than one light source. In some cases, the light sources may be configured to illuminate the microparticles with light having different wavelengths or wavelength bands (e.g., blue light and green light). In some embodiments, the light sources may be configured to illuminate the microparticles at different directions.

Light scattered forwardly from the microparticles may be directed to detection system 16 by folding mirror 18 or another such light directing component. Alternatively, detection system 16 may be placed directly in the path of the forwardly scattered light. In this manner, the folding mirror or other light directing components may not be included in the system. In one embodiment, the forwardly scattered light may be light scattered by the microparticles at an angle of about 180° from the direction of illumination by light source 14, as shown in FIG. 5. The angle of the forwardly scattered light may not be exactly 180° from the direction of illumination such that incident light from the light source may not impinge upon the photosensitive surface of the detection system. For example, the forwardly scattered light may be light scattered by the microparticles at angles less than or greater than 180° from the direction of illumination (e.g., light scattered at an angle of about 170°, about 175°, about 185°, or about 190°).

Light scattered by the microparticles at an angle of about 90° from the direction of illumination may also be collected. In one embodiment, this scattered light may be separated into more than one beam of light by one or more beamsplitters or dichroic mirrors. For example, light scattered at an angle of about 90° to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the microparticles.

Scattered light detected by detection system 16 and/or detection system 26 may generally be proportional to the volume of the microparticles that are illuminated by the light source. Therefore, output signals of detection system 16 and/or output signals of detection system 26 may be used to determine a diameter and/or volume of the microparticles that are in the illumination zone or detection window. In addition, the output signals of detection system 16 and/or detection system 26 may be used to identify more than one microparticle that are stuck together or that are passing through the illumination zone at approximately the same time. Therefore, such microparticles may be distinguished from other sample microparticles and calibration microparticles. Furthermore, the output signals of detection system 16 and/or detection system 26 may be used to distinguish between sample microparticles and calibration microparticles.

The other three beams of light may be directed to detection systems 28, 30, and 32. Detection systems 28, 30, and 32 may be configured to detect fluorescence emitted by the microparticles. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence. In some embodiments, spectral filters 34, 36, and 38 may be coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

Each of the detector's output currents is proportional to the fluorescent light impinging on it and results in a current pulse. The current pulse may be converted to a voltage pulse, low pass filtered, and then digitized by an A/D converter. The conversion, filtering, and digitizing may be performed using any suitable components known in the art. The detection systems that are used to determine an identity of the sample microparticles as described below (e.g., detection systems 28 and 30) may be avalanche photodiodes (APDs), a photomultiplier tube (PMT), or another photodetector. The detection system that is used to identify a reaction taking place on the surface of the microparticles (e.g., detection system 32) may be a PMT, an APD, or another form of photodetector.

Although the system of FIG. 5 is shown and described below to include two detection systems having two different detection windows for distinguishing between microparticles having different dye characteristics, it is to be understood that the system may include more than two such detection windows (i.e., 3 detection windows, 4 detection windows, etc.). In such embodiments, the system may include additional beamsplitters and additional detection systems having other detection windows. In addition, spectral filters and/or lenses may be coupled to each of the additional detection systems. In another embodiment, the system may include two or more detection systems configured to distinguish between different materials that are reacted on the surface of the microparticles. The different reactant materials may have dye characteristics that are different than the dye characteristics of the microparticles.

The system may also include processor 40. Processor 40 may be coupled to the detectors by one or more transmission media and optionally one or more components interposed between the processor and the detectors. For example, processor 40 may be coupled to detection system 26 by transmission medium 42. The transmission medium may include any suitable transmission medium known in the art and may include "wired" and "wireless" portions. The processor may include, in one example, a DSP that is configured to integrate the area under the pulse to provide a number which represents the magnitude of the fluorescence. The processor may also be configured to perform one or more of the steps of the embodiments described herein.

In some embodiments, the output signals generated from fluorescence emitted by the microparticles may be used to determine an identity of the microparticles and information about a reaction taking place on the surface of the microparticles. For example, output signals of two of the detection systems may be used to determine an identity of the microparticles as described herein, and output signals of the other detection system may be used to determine a reaction taking or taken place on the surface of the microparticles. Therefore, the selection of the detectors and the spectral filters may vary depending on the type of dyes incorporated into or bound to the microparticles and/or the reaction being measured (i.e., the dye(s) incorporated into or bound to the reactants involved in the reaction). The values generated by detections systems 16, 26, 28, 30, and 32 may be used in the methods described herein.

The system shown in FIG. 5 is configured to classify microparticles according to embodiments described herein. In some embodiments, the system may include storage medium 44. Storage medium 44 may include look-up table 46 as well as program instructions 45. The storage medium and the look-up table may be configured as described herein. In some embodiments, processor 40 may be configured to classify a microparticle using look-up table 46 in combination with data acquired for the microparticle. The data may be acquired as described herein. In this manner, a processor of a measurement system may be configured to classify microparticles as described herein. Alternatively, a processor that is not actually a part of the measurement system but is coupled to the measurement system (e.g., by a transmission medium) such as a processor of a stand-alone computer system may be configured to classify microparticles as described herein.

Program instructions implementing methods such as those described herein may be transmitted over or stored on a storage medium (e.g., storage medium 44). The storage medium may include but is not limited to a read-only memory, a random access memory, a magnetic or optical disk, or a magnetic tape. In an embodiment, a processor such as processor 40 may be configured to execute the program instructions to perform a computer-implemented method according to the above embodiments. The processor may take various forms, including a personal computer system, mainframe computer system, workstation, network appliance, Internet appliance, personal digital assistant (PDA), a digital signal processor (DSP), field programmable gate array (FPGA), or other device. In general, the term "computer system" may be broadly defined to encompass any device having one or more processors, which executes instructions from a memory medium. The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

It will be appreciated to those skilled in the art having the benefit of this disclosure that this invention is believed to provide methods, data structures, and systems for classifying microparticles. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method comprising:

acquiring a first set of data corresponding to measurable parameters of a microparticle, wherein the first set of data is generated via a flow cytometer or a fluorescent imaging system;

accessing a look-up table framed by values associated with at least one of the measurable parameters, wherein the look-up table comprises a plurality of locations, at least some of which are associated with one or more predefined algorithms, wherein each predefined algorithm is indicative of a different microparticle classification;

identifying a location of the look-up table to which the first set of data corresponds;

processing only the one or more predefined algorithms, which are associated with the identified location, to determine whether the first set of data fits at least one of the one or more predefined algorithms; and after said identifying and processing steps, classifying the microparticle within at least one predefined categorization based upon the step of processing only the one or more predefined algorithms associated with the identified location.

2. The method of claim 1, wherein the step of classifying the microparticle comprises one of:

classifying the microparticle within at least one of the microparticle classifications upon determining the first set of data fits a predefined algorithm associated with the at least one microparticle classification; and classifying the microparticle within a reject classification upon determining the first set of data does not fit the one or more predefined algorithms.

3. The method of claim 1, wherein the step of processing only the one or more predefined algorithms comprises iteratively processing the first set of data within the one or more predefined algorithms associated with the identified location until the first set of data is classified into a predefined categorization.

4. The method of claim 1, wherein the step of classifying the microparticle comprises classifying the microparticle within multiple microparticle classifications upon determining the first set of data fits a plurality of the one or more predefined algorithms associated with the identified location.

5. The method of claim 4, further comprising:

determining a single predefined algorithm of the plurality of predefined algorithms that bests fits the first set of data; and cataloging the microparticle within the microparticle classification associated with the single predefined algorithm.

6. The method of claim 1, wherein the step of identifying the location of the look-up table comprises identifying a coarse location of the look-up table.

7. The method of claim 1, further comprising creating a second data set prior to the step of identifying the location of the look-up table, wherein the second data set comprises one or more umbrella values respectively correlating to one or more distinct values of the first set of data, wherein each of the umbrella values represents a range of possible values for a corresponding measurable parameter, wherein the look-up table is framed by umbrella values of at least one of the measurable parameters, and wherein the subsequent step of identifying the location of the look-up table comprises identifying the location of the look-up table to which the second data set corresponds.

8. A system, comprising:

a processor;

a look-up table framed by one or more measurable parameters of microparticles, wherein the look-up table comprises a plurality of locations, at least some of which are associated with one or more predefined algorithms, wherein each predefined algorithm is indicative of a different microparticle classification; and a storage medium comprising program instructions which are executable by the processor for:

acquiring a set of data corresponding to measurable parameters of a microparticle, wherein the set of data is generated via a flow cytometer or a fluorescent imaging system;

identifying a location of the look-up table to which the set of data corresponds;

processing only the one or more predefined algorithms, which are associated with the identified location, to determine whether the set of data fits at least one of the one or more predefined algorithms; and after said identifying and processing steps, classifying the microparticle within at least one predefined categorization based upon the step of processing only the one or more predefined algorithms associated with the identified location.

9. The system of claim 8, wherein the program instructions for classifying the microparticle comprises program instructions for:

classifying the microparticle within at least one of the microparticle classifications upon determining the set of data fits a predefined algorithm associated with the at least one microparticle classification; and classifying the microparticle within a reject classification upon determining the set of data does not fit the one or more predefined algorithms.

10. The system of claim 8, wherein the program instructions for processing only the one or more predefined algorithms comprises program instructions for iteratively processing the set of data within the one or more predefined algorithms associated with the identified location until the set of data is classified into a predefined categorization.

11. The system of claim 8, wherein the program instructions for classifying the microparticle comprises program instructions for classifying the microparticle within multiple microparticle classifications upon determining the set of data fits a plurality of the one or more predefined algorithms associated with the identified location.

12. The system of claim 8, wherein the look-up table is formulated by less than all of the measurable parameters associated with the set of data.

13. The system of claim 8, wherein the look-up table is formulated by more than two measurable parameters associated with set of data.

14. The system of claim 8, wherein the look-up table is formulated by umbrella values of at least one of the measurable parameters, and wherein each of the umbrella values represent a range of possible values for a corresponding measurable parameter.

15. The system of claim 14, wherein the number of umbrella values associated with at least two of the measurable parameters formulating the look-up table are different.

16. The system of claim 8, wherein the storage medium comprises the look-up table.

17. A computer-implemented method, comprising:

acquiring a first set of data corresponding to measurable parameters of a microparticle, wherein the first set of data is generated via a flow cytometer or a fluorescent imaging system;

creating a second data set comprising one or more umbrella values respectively correlating to one or more distinct values of the first set of data, wherein each of the umbrella values represents a range of possible values for a corresponding measurable parameter;

identifying a location of a look-up table to which the second data set corresponds, wherein the look-up table is framed by umbrella values of at least one of the measurable parameters;

determining whether the first set of data fits a predefined algorithm indicative of a microparticle classification associated with the identified location of the look-up table; and classifying the microparticle within at least one predefined categorization based upon determining whether the first set of data fits the predefined algorithm.

18. The method of claim 17, wherein the ranges of possible values associated with umbrella values of at least one of the measurable parameters framing the look-up table are non-uniform.

19. The method of claim 17, wherein the step of classifying the microparticle comprises one of:

classifying the microparticle within the microparticle classification upon determining the first set of data fits the predefined algorithm; and classifying the microparticle within a reject classification upon determining the first set of data does not fit within the predefined algorithm.

20. The method of claim 17, further comprising determining whether the first set of data fits into one or more additional predefined algorithms respectively indicative of one or more different microparticle classifications associated with the identified location of the look-up table, wherein the step of classifying the microparticle within at least one predefined categorization is further based upon determining whether the first set of data fits the one or more additional predefined algorithms.

* * * * *